United States Patent [19]

Aoki et al.

[11] Patent Number: 5,414,191
[45] Date of Patent: May 9, 1995

[54] METHOD OF REMOVING ALKYLTETRALINS FROM AN ALKYLBENZENE MIXTURE

[75] Inventors: Seiji Aoki; Tomonori Kato; Hiroaki Taniguchi; Hidetosi Morotomi; Masami Ono, all of Tokyo, Japan

[73] Assignees: NKK Corporation, Japan; Vista Chemical Company, Houston, Tex.

[21] Appl. No.: 182,676

[22] Filed: Jan. 14, 1994

Related U.S. Application Data

[63] Continuation of Ser. No. 12,890, Feb. 3, 1993, abandoned.

[30] Foreign Application Priority Data

Feb. 13, 1992 [JP] Japan .................................. 4-026809

[51] Int. Cl.⁶ ............................................... C07C 7/12
[52] U.S. Cl. ................................ 585/820; 585/822; 585/828; 585/831
[58] Field of Search ................ 585/820, 822, 828, 831

[56] References Cited

U.S. PATENT DOCUMENTS 3,954,895 5/1976 Shima et al. ..................... 585/452
4,992,622 2/1991 Shiroto et al. ..................... 585/828

FOREIGN PATENT DOCUMENTS 9003960 4/1990 WIPO .
9003961 4/1990 WIPO .

*Primary Examiner*—Anthony McFarlane
*Assistant Examiner*—Nhat D. Phan
*Attorney, Agent, or Firm*—Browning, Bushman, Anderson & Brookhart

[57] ABSTRACT

According to the method of the invention, it is possible to separate and selectively remove alkyltetralins coexisting in a small amount in a LAB mixture which is an intermediate raw material for surfactants for detergents, the method conveniently being carried out in a continuous manner using a solid adsorbent.

10 Claims, 3 Drawing Sheets

METHOD OF REMOVING ALKYLTETRALINS FROM AN ALKYLBENZENE MIXTURE

This is a continuation of U.S. application Ser. No. 08/012,890, field Feb. 3, 1993, now abandoned.

BACKGROUND OF THE INVENTION

1. Field of the Invention

This invention relates to a method of removing alkyltetralins coexisting in linear alkylbenzene (LAB) which is an intermediate raw material in making linear alkylbenzene sulfonate (LAS), a surfactant useful as a detergent for household and industrial use.

2. Description of the Prior Art

Presently, the surfactant LAS is used as a detergent for industrial use and/or household use on a large scale in the world including Japan, and manufactured by chlorinating n-paraffins of $C_{10}$–$C_{14}$ separated from the kerosene fraction of petroleum to obtain the chlorinated n-paraffins. The chlorinated n-paraffins are reacted with benzene as an alkylating agent and sulfonated to obtain LAS.

Recently, it was found, during the alkylation reaction to produce the LAB, that some of the side chain alkyl groups are cyclized, as a side reaction, to produce alkyltetraline (AT) skeletons. The biodegradation rate of the alkyltetralins is slower than that of LAB's.

However, to date no practical technique for separating and removing the alkyltetralins contained in LAB has been developed.

As mentioned above, the biodegradation rate of the alkyltetralins is slow. On the other hand, since the production of LAS is so great in quantity, it is desirable, to minimize environmental problems, to minimize the presence of the alkyltetralins. However, no practical means capable of removing the alkyltetralins from LAS has been developed.

SUMMARY OF THE INVENTION

An object of the invention is to provide a means for removing the alkyltetralins from LAB efficiently.

The present inventors have investigated various ways to achieve the above object. It was found to be substantially difficult to separate alkyltetralins alone, i.e. selectively, from LAB by distillation, crystallization, extraction or the like, because LAB is a mixture of many components of chemically structural similarity to each other as well as the alkyltetralins. Thereupon, the inventors have further continued the investigation. As a result, they have found an adsorbent which exhibits a great difference in adsorbtivity between LAB and alkyltetralins as a whole even though respective ones are a mixture of many components. The adsorbent adsorbs more strongly alkyltetralins and therefore the alkylbenzenes should be removed only in small amounts. The preferred adsorbent has a separation coefficient such that $\alpha_{AT}^{LAB} \geq 1.75$, although adsorbents having an $\alpha_{AT}^{LAB}$ of $\geq 2$ will function. They also found that the alkyltetralins can be removed efficiently from LAB by using the adsorbent to complete the present invention.

Thus, the present invention relates to a method of removing alkyltetralins present in alkylbenzenes which comprises contacting alkylbenzenes, wherein the alkyl group contains from 10 to 14 carbon, containing alkyltetralins as contaminants with an adsorbent having a separation coefficient $\alpha_{AT}^{LAB}$ of not less than 1.75, and separating the raffinate from the adsorbent.

DESCRIPTION OF THE PREFERRED EMBODIMENT

Figure 1:
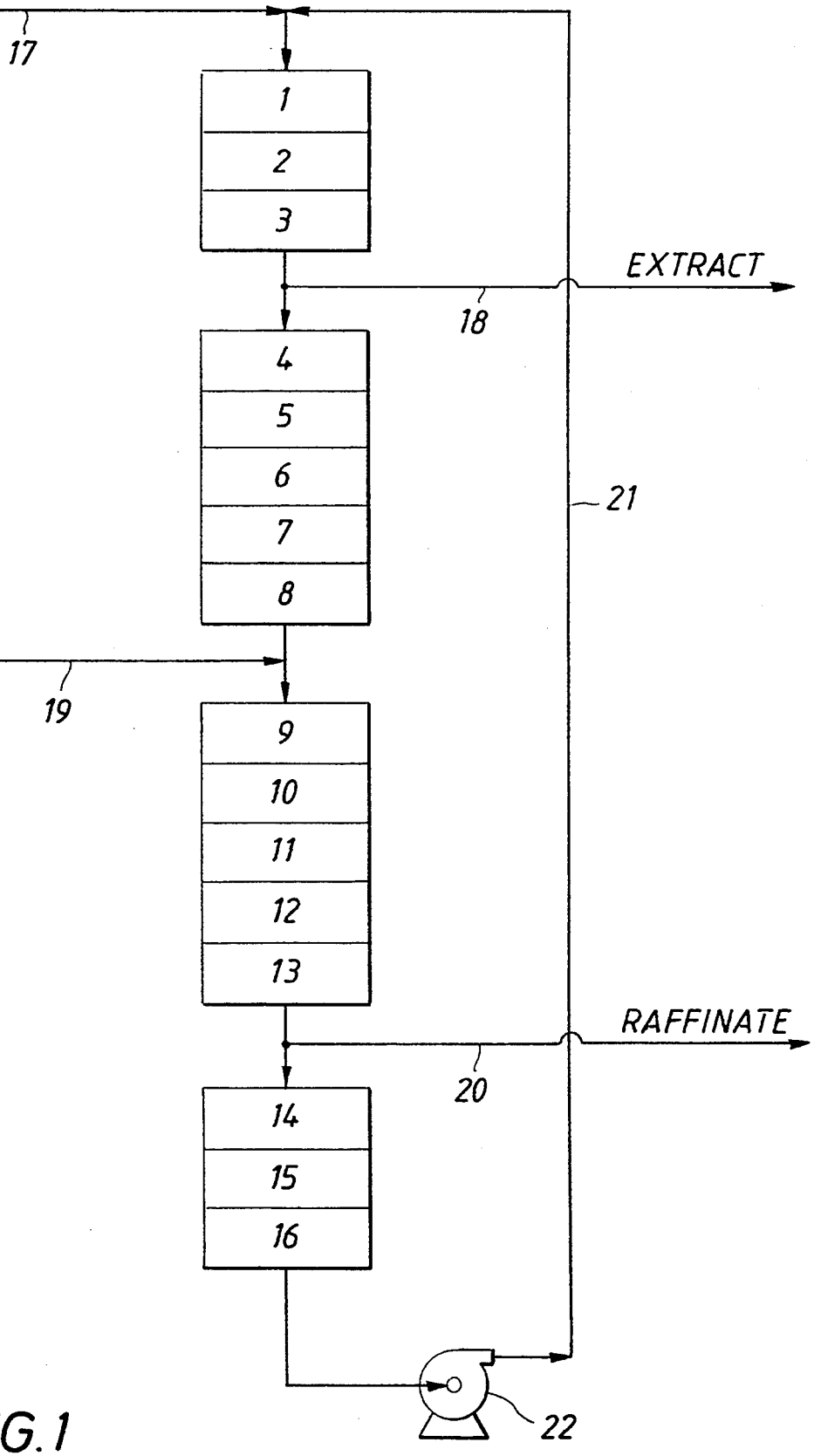
FIG. 1 is a block diagram showing an outline of the apparatus used in an example of the invention.

The linear alkylbenzene to be purified by the method of the invention may be used in general as a raw material for the production of LAS, and is a mixture of linear alkylbenzenes of which the number of carbon atoms of the alkyl group is 10–. The linear alkylbenzenes may be obtained by chlorinating n-paraffins of $C_{10}$–$C_{14}$ range which have been separated from the kerosene fraction of petroleum and reacting the chlorinated n-paraffin with benzene as an alkylating agent. The content of alkyltetralins in the alkylbenzenes is usually about 1–20 wt. %.

As the adsorbent, that having a separation coefficient $\alpha_{AT}^{LAB}$, defined by the following formulas, of preferably not less than 1.75 is selected and used:

$$\text{Equilibrium Constant } Ki = \frac{\text{Weight Concentration of Component } i \text{ in Extract}}{\text{Weight Concentration of Component } i \text{ in Raffinate}} \quad \text{I.}$$

$$\text{Separation Coefficient } \alpha_{AT}^{LAB} = \frac{\text{Equilibrium Constant } K_{AT} \text{ of Alkyltetralin}}{\text{Equilibrium constant } K_{LAB} \text{ of Linear Alkylbenzene}} \quad \text{II.}$$

The equilibrium constant Ki is determined by putting each adsorbent into a mixture of LAB and akyltetralin (AT), and after reaching an equilibrium state, the liquid phase is separated as a raffinate. Subsequently, after washing the adsorbent, adsorbed components are eluted as an extract, and LAB and AT are analyzed quantitatively as to the liquid phase (raffinate) and the extract. As the analytical means, gas chromatography may be used. The equilibrium constant of AT is calculated frown the weight concentration of AT in the extract and the weight concentration of AT in the raffinate obtained by the quantitative analysis according to the above formula, and the equilibrium constant of LAB is calculated from the weight concentration of LAB in the extract and the weight concentration of LAB in the raffinate. The separation coefficient can be calculated from both equilibrium constants according to the above formulas.

As such an adsorbent, any material may be used which is a porous solid material, which does not react with the raw materials or the desorbent, and does not deteriorate nor act as a reaction catalyst, under adsorption conditions, and which has a suitable difference between the adsorptivity of LAB and the adsorptivity of AT onto the surface, i.e., preferably has a separation coefficient $\alpha_{AT}^{LAB} \geq 1.75$. Zeolites substituted with metals are preferred, and zeolites substituted with alkali metals and/or alkaline earth metals are particularly preferred. The most preferable metals are Na and K, the most preferable zeolite being zeolite Y, a synthetic zeolite.

The desorbent for desorbing or eluting AT, etc. adsorbed on the adsorbent may be any liquid having an ability to desorb them. When the present method is conducted in the pseudo-moving bed method described later, the preferred desorbents are materials (low boiling point materials are desirable) having a boiling point greatly different from ATs and LABs to facilitate recovery after separation. Suitable desorbents includes aliphatic hydrocarbons, such as n-octane, n-nonane and n-decane, naphthenes, such as cyclo-hexane, methylcyclohexane and decalin, and aromatic hydrocarbons, such as benzene, toluene, xylene, n-butylbenzene, sec-butylbenzene, tert-butylbenzene, p-diethylbenzene, n-pentylbenzene and n-hexylbenzene. The desorbent is preferably a single material, as opposed to a mixture, in view of simplifying the entire process, but it is also possible to prepare a desorbent satisfying the above conditions by mixing some materials, different in their adsorptivity, at a suitable ratio. As such a mixed desorbent a mixture of aliphatic hydrocarbon(s) and aromatic hydrocarbon(s) of which the adsorptivity is adjusted by the mixing ratio can be used. Furthermore, alcohols or ketones can be mixed in order to adjust the adsorptivity.

On the other hand, when a batch-wise method is used for removing alkyltetralins from LAB, it is preferred that the adsorbent selected have a separation coefficient $\alpha_{AT}{}^{LAB}$ as great as possible, and that the desorbent for removing the adsorbed alkyltetralins have an adsorptivity stronger than the alkyltetralins and a boiling point as low as possible so that its removal from the adsorbent can be conducted by heating and/or pressure drop, etc. In view of considering also availability and cost, examples of preferable desorbents for batch operations are benzene, toluene, xylene, and so on.

As one process for conducting the method of the invention, for example, the pseudo-moving bed continuous adsorption separating process is suitable. This process is well understood by those skilled in the art and is industrially used in the separation of pure p-xylene frown a xylene mixture. In this method, at least four adsorption vessels, preferably not less than eight vessels, packed with the adsorbent are used, and delivered raw materials and desorbent continuously flow therethrough. Respective vessels are provided with exit ports for extract and raffinate. The delivery into and taking out from each vessel is conducted by valves attached to each vessel separately or by multiport valves which connect a plurality of tubes and control them.

In such a moving bed process and apparatus, it is possible to conduct a process wherein the adsorbent appears to move continuously and to contact the delivered or feed raw material and the desorbent continuously in a countercurrent system by moving the delivery position and the taking out or exit position, respectively, successively at a prescribed step time. According to the process, the raw material to be separated is quantitatively continuously supplied, and the raffinate, extract obtained by the separation using adsorption are also continuously taken out.

The changeover and control of the above step time is usually conducted by an automated system, as the number of the adsorption vessels usually is at least eight vessels or more. The number of vessels varies according to the difficulty of separation, but 50 vessels or stages or more is generally uneconomical.

Each adsorption vessel may be in an independent form or may be formed by providing partitions in a single, large vessel. The orientation may be vertical or horizontal.

As noted, the pseudo-moving bed adsorption separating process is well known as it is conducted industrially on a large scale for separating pure p-xylene from a xylene mixture.

Another very suitable method for conducting a substantially continuous process involves using a plurality of adsorption towers packed with the adsorbent, and intermittently repeating a cycle of steps at each tower. In this method the following steps are used:

1. the linear alkylbenzene (raw material) is supplied as the raw material to one side of the adsorption tower to adsorb the alkyltetralins selectively, and the linear alkylbenzene from which the alkyltetralins have been removed are taken out from the other side. This is the adsorption separating step.;
2. the supply liquid, i.e., the raw material, is stopped prior to leakage or breakthrough of the alkyltetralins from the adsorbent and, the supply liquid is changed to a desorbent to recover the linear alkylbenzene remaining in the adsorption tower and the adsorbed alkyltetralins. This is the substitution process step;
3. the desorbent is recovered from the adsorbent by heating or reducing the pressure of the cycle in the plurality of vessels. This is the solvent recovery step.

The embodiment of the invention is not limited to the aforementioned methods, but it is possible to use various other processes.

The alkyltetralins content of the linear alkylbenzene purified by the method of the invention can be reduced to not more than 10% by weight of the raw material, and can be reduced to not more than 1 wt. %, preferably not more than 0.5 wt. %.

In the method of the invention, alkyltetralins are selectively removed by adsorption using a particular adsorbent to obtain alkylbenzenes in a high purity. As the adsorbent, zeolite which is known as molecular sieves, can preferably be used. However, as can be seen frown the gas chromatograms of FIG. 3 and FIG. 4, both the extract and raffinate are a mixture of numerous compounds, and their molecular weights overlap. Accordingly, it is apparent that the adsorbent employed in the invention does not solely utilize the relation between the pore size and the molecular size. It is not clear what function induces the separation ability, i.e. the separation process is not totally understood.

EXAMPLE 1

Figure 2:
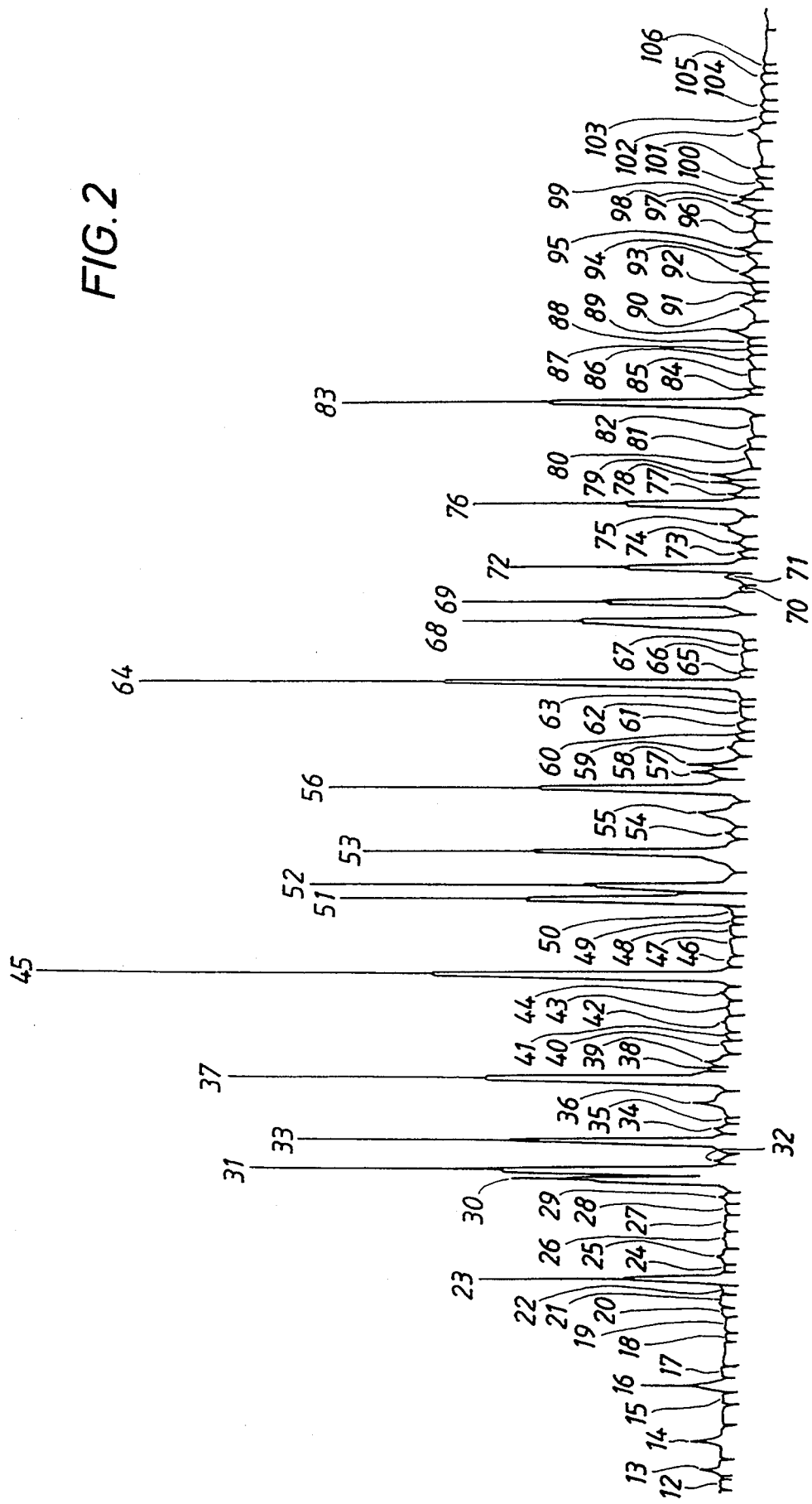
FIG. 2 is a gas chromatogram of the composition of the raw material.
Figure 3:
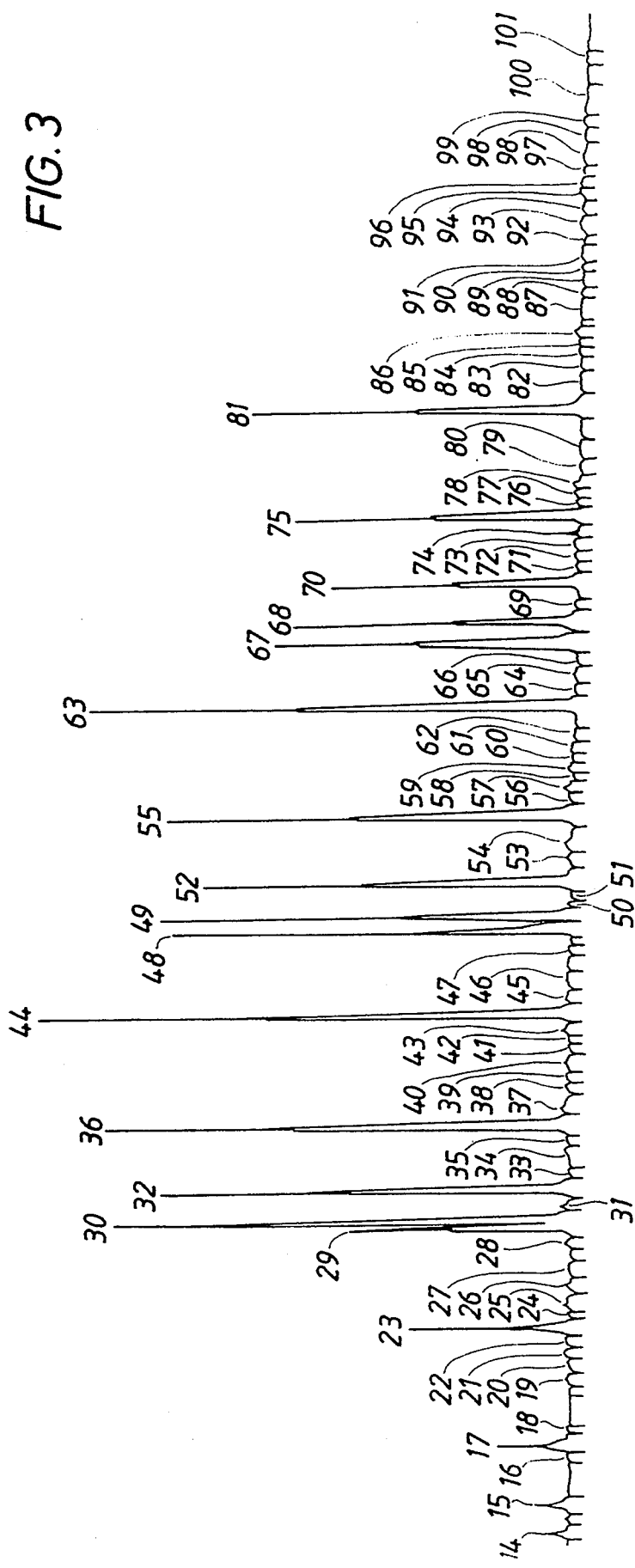
FIG. 3 is a gas chromatogram of the raffinate separated from the raw material shown in FIG. 2.
Figure 4:
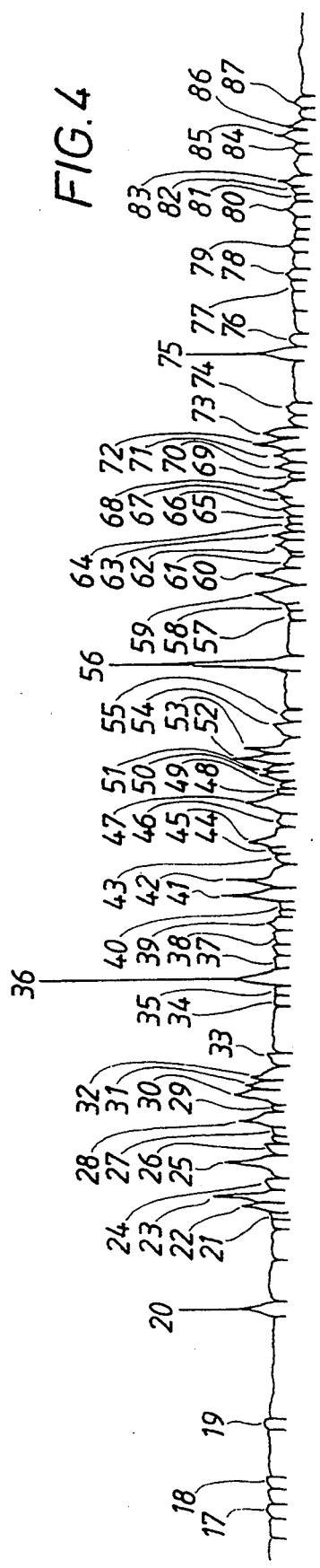
FIG. 4 is a gas chromatogram of the extract separated from the raw material shown in FIG. 2.

Four parts by weight of a commercial Na—Y form of zeolite ($SiO_2/Al_2O_3 = 5$ grain size: 40–80 mesh) was calcined at 350° C. for 2 hours and dried and 10 parts by weight of a raw material of LAB/AT=90/10 (weight ratio) were put in a 50 ml Erlenmeyer flask with a ground stopper. Equilibrium was reached by shaking for 4 hours with heating at 140° C. Subsequently, the liquid phase (raffinate) and the solid phase were separated by filtration, washing and extraction of the adsorbed material (extract), and each composition was analyzed by using a gas chromatograph. The relative separation sufficient was calculated, and it was found that the relative separation coefficient of LAB on the basis of AT $\alpha_{AT}{}^{LAB}$ was 10.0. Gas chromatograms of the raffinate and extract obtained by the one step treatment and the raw material to be treated are shown in FIG. 3, FIG. 4 and FIG. 2, respectively. It is apparent that LAB and AT were separated by the adsorption treatment from these figures.

EXAMPLE 2

Quite the same adsorption equilibrium experiment as Example 1 was conducted, except that a K—Y form of zeolite ($SiO_2/Al_2O_3=5$, grain size: 40–80 mesh, ion exchange ratio: 99%) was calcined at 350° C. for two hours, dried and used instead of the Na—Y form of zeolite. The relative separate on coefficient of LAB based on AT $\alpha_{AT}^{LAB}$ was 4.5.

EXAMPLE 3–18

Four pans by weight of a commercial Na—Y form zeolite ($SiO_2/Al_2O_3=5$, grain size: 40–80 mesh) was calcined at 350° C. for two hours and dried. Two parts by weight of a raw material of LAB/AT=90/10 (weight ratio) and eight parts by weight of a material shown in Table 1 as the desorbent were put in a 50 ml Erlenmeyer flask with ground stopper, and were shaken for four hours with heating. Subsequently, the relative separation coefficient of LAB based on AT was calculated by the method similar to Example 1. The results are shown in Table 1.

TABLE 1

| | Desorbent | $\alpha_{AT}^{LAB}$ |
|---|---|---|
| Example 3 | tert-Butylbenzene | 4.4 |
| Example 4 | n-Dodecane | 16.7 |
| Example 5 | Cyclohexane | 18.4 |
| Example 6 | Methylcyclohexane | 14.6 |
| Example 7 | t-Decalin | 10.6 |
| Example 8 | n-Nonane | 16.5 |
| Example 9 | p-Cymene | 3.4 |
| Example 10 | Diisopropylbenzene(mixture) | 6.6 |
| Example 11 | m-Diisopropylbenzene | 7.8 |
| Example 12 | p-Diisopropylbenzene | 7.1 |
| Example 13 | p-Diethylbenzene | 6.6 |
| Example 14 | n-Hexylbenzene | 21.2 |
| Example 15 | Diethylbenzene/n-Dodecane = 2/98 | 13.2 |
| Example 16 | Diethylbenzene/n-Dodecane = 10/90 | 13.5 |
| Example 17 | Diethylbenzene/n-Dodecane = 30/70 | 12.8 |
| Example 18 | Diethylbenzene/n-Dodecane = 50/50 | 14.2 |

EXAMPLE 19

The separation of LAB and AT by adsorption was conducted using the pseudo-moving bed type continuous adsorption separating apparatus shown in FIG. 1. AT in the raw material was 10%. The Na—Y form zeolite used in Example 1 was used as the adsorbent, and t-butylbenzene was used as the desorbent. The adsorbent was packed in columns (1–16) having a loading capacity of 70 ml. The crude LAB was supplied at 50 ml/hr from line 19 as the raw material, and the desorbent was supplied at 186 ml/hr from line 17. On the other hand, the extract was taken out at 142 ml/hr from line 18, and the raffinate was taken out at 94 ml/hr from line 20, respectively. The changeover of each supply line and taking out line (each line was transferred in the liquid flow direction by one column simultaneously) was conducted at an interval of 360 seconds. LAB was obtained from the raffinate, and the purity was 99% on the basis free from the desorbent. The recovery was 95%.

What is claimed is:

1. A method of removing alkyltetralins present in alkylbenzenes which comprises contacting a linear alkylbenzene mixture containing alkyltetralins as contaminants with an absorbent for adsorbing said alkyltetralins to produce a raffinate having a reduced content of alkyltetralins and an extract adsorbed on said adsorbent, and separating said raffinate from said adsorbent containing said extract, said adsorbent comprising a zeolite substituted with a metal and having a separation coefficient $\alpha_{AT}^{LAB}$ defined as follows:

$$\text{Separation Coefficient } \alpha_{AT}^{LAB} = \frac{K_{AT}}{K_{LAB}}$$

wherein $$K_{AT} = \frac{\text{Weight Concentration of Alkyltetralins in said Extract}}{\text{Weigh Concentration of Alkyltetralins in said Raffinate}}$$

and $$K_{LAB} = \frac{\text{Weight Concentration of Linear Alkylbenzenes in said Extract}}{\text{Weight Concentration of Linear Alkylbenzenes in said Raffinate}}$$

and wherein $\alpha_{AT}^{LAB}$ is not less than about 1.75.

2. The method of claim 1 wherein the alkyl groups of said alkylbenzenes have from 10 to 14 carbon atoms.

3. The method of claim 1 which is conducted in a substantially continuous fashion by using a plurality of adsorption towers packed with said adsorbent and at each tower intermittently repeating the cycle comprising:

a. supplying said alkylbenzene mixture as raw material to a first side of said adsorption tower and removing from a second side of said adsorption tower said raffinate, b. stopping the introduction of said raw material to said tower prior to adsorbed alkyltetralins leaking from said adsorbent and introducing a desorbent liquid to remove linear alkylbenzenes remaining in said adsorption tower and desorb said alkyltetralins from said adsorbent to produce a desorbent mixture of desorbent, linear alkylbenzenes and alkyltetralins; and c. recovering said desorbent liquid from said desorbent mixture.

4. The method of claim 1 comprising using a pseudo-moving bed process to remove said alkyltetralins from said alkylbenzene mixture.

5. The method of claim 1 wherein said adsorbent comprises an alkali metal substituted Y zeolite.

6. The method of claim 1 wherein said metal comprises an alkali metal.

7. The method of claim 1 wherein said metal comprises an alkaline earth metal.

8. The method of claim 7 wherein said zeolite is a Y zeolite.

9. The method of claim 1 wherein said metal is sodium.

10. The method of claim 1 wherein said metal is potassium.

* * * * *

UNITED STATES PATENT AND TRADEMARK OFFICE
CERTIFICATE OF CORRECTION

PATENT NO. : 5,414,191
DATED : May 9, 1995
INVENTOR(S) : Seiji Aoki; Tomonori Kato; Hiroaki Taniguchi; Hidetosi Morotomi; Masami Ono It is certified that error appears in the above-indentified patent and that said Letters Patent is hereby corrected as shown below:

In column 1, lines 26-27, delete "alkyltetraline" and insert therefor --alkyltetralin".
In column 2, line 49, delete "frown" and insert therefor --from--.
In column 3, line 3, insert a comma after "etc.".
In column 3, line 10, delete "includes" and insert therefor --include--.
In column 3, line 22, insert --of-- before "a mixture".
In column 3, line 42, delete "frown" and insert therefor --from--.
In column 3, line 60, delete the comma after "raffinate".
In column 4, line 19, delete the period after "step".
In column 4, line 22, delete the comma after "and" and insert a comma after "adsorbent".
In column 4, line 42, insert a comma after "zeolite".
In column 4, line 44, delete "frown" and insert therefor --from--.
In column 5, line 13, delete "separate on" and insert therefor --separation--.
In column 5, line 16, delete "pans" and insert therefor --parts--.
In column 5, line 54, delete "t-butylbenzene" and insert therefor --tert-butylbenzene".
In column 6, line 7, delete "absorbent" and insert therefor --adsorbent--.
In column 6, line 39, delete the comma and insert therefor a semicolon.

Signed and Sealed this

Eleventh Day of July, 1995

Attest:

BRUCE LEHMAN

Attesting Officer     Commissioner of Patents and Trademarks